United States Patent [19]

Fisher et al.

[11] Patent Number: 5,514,639
[45] Date of Patent: May 7, 1996

[54] AGRICULTURAL COMPOSITIONS COMPRISING PH BUFFERS, PH INDICATORS, AND PH SENSITIVE AGROCHEMICALS

[75] Inventors: Jonah Fisher; Martin D. Bloomberg, both of Lower Houghton, South Africa

[73] Assignee: Gouws & Scheepers (Proprietary) Limited, South Africa

[21] Appl. No.: 130,459

[22] Filed: Oct. 1, 1993

Related U.S. Application Data

[62] Division of Ser. No. 690,395, Apr. 25, 1991, Pat. No. 5,278,132, which is a continuation of Ser. No. 12,027, Feb. 9, 1987, abandoned.

[30] Foreign Application Priority Data

Feb. 11, 1986 [ZA] South Africa ............................ 86/0994

[51] Int. Cl.$^6$ ..................................................... A01N 25/22
[52] U.S. Cl. ........................ 504/116; 504/250; 504/251; 514/84; 514/119; 514/120; 514/132; 514/144; 514/394; 514/425; 514/477; 514/521; 514/564; 514/726; 514/772; 514/784; 514/788
[58] Field of Search ............................ 504/116; 424/405; 514/84; 71/DIG. 1

[56] References Cited

U.S. PATENT DOCUMENTS

| | | | |
|---|---|---|---|
| 2,599,697 | 6/1952 | Conklin | 23/230 |
| 2,758,115 | 8/1956 | Lorenz | 260/248 |
| 3,244,502 | 4/1966 | Woogerd et al. | 71/2.4 |
| 3,770,641 | 10/1973 | Cantor et al. | 252/90 |
| 4,062,649 | 12/1977 | Kuderna et al. | 23/230 R |
| 4,214,888 | 7/1980 | Young | 71/28 |

FOREIGN PATENT DOCUMENTS

| | | |
|---|---|---|
| 163523 | 7/1976 | Czechoslovakia . |
| 16578 | 10/1980 | European Pat. Off. . |
| 2108419 | 5/1972 | France . |
| 2217403 | 9/1974 | France . |
| 1329449 | 9/1973 | United Kingdom . |
| 1500850 | 2/1978 | United Kingdom . |
| 2085582 | 4/1982 | United Kingdom . |

OTHER PUBLICATIONS

*The Agrochemicals Handbook* "Azinphos–Methyl", 1983.
Merck Index, p. MISC–104, "Indicators", and entry 5169 Lacmoid, 1983.
Chem. Abst.96:36828x 1982.
Chem. Abst. 98:1682j 1983.
Chem. Abst. 89:141919f 1978.
*The Merck Index.* Tenth Edition, Monograph Nos. 4060, 4062 and 5975 (1983).

*Primary Examiner*—S. Mark Clardy
*Attorney, Agent, or Firm*—Rothwell, Figg, Ernst & Kurz

[57] ABSTRACT

The invention provides a concentrate for dilution with water in the preparation of an agrigulatural composition for application to crops, soil or animals and comprising an agricultural chemical whose agricultural activity varies with the pH of the water; and the invention provides a method of preparing such agricultural composition by mixing the concentrate with water and effecting such pH modification to the composition as is necessary to obtain a pH in the composition at which the agricultural activity of the chemical is acceptable. The concentrate comprises an active ingredient and a pH indicator for colouring the water, and the proportions of pH indicator and active ingredient are selected so that when the concentrate is diluted with water to provide an effective concentration of active ingredient in the water, the pH indicator indicates visually whether or not the pH of the water is suitable for acceptable agricultural activiy of the chemical.

20 Claims, No Drawings

AGRICULTURAL COMPOSITIONS COMPRISING PH BUFFERS, PH INDICATORS, AND PH SENSITIVE AGROCHEMICALS

This is a division of application Ser. No. 07/690,395, filed Apr. 25, 1991, now U.S. Pat. No. 5,278,132, which is a continuation of Ser. No. 07/012,027, filed Feb. 9, 1987, now abandoned.

This invention relates, broadly, to agricultural compositions. More particular it relates to a concentrate for dilution with water in the preparation of an agricultural composition for application to crops, soil or animals and comprising an agricultural chemical whose agricultural activity varies with the pH of the water, and to a method of formulating such agricultural composition.

In accordance with the invention there is provided a concentrate for dilution with water in the preparation of an agricultural composition for application to crops, soil or animals and comprising an agricultural chemical whose agricultural activity varies with the pH of the water, the concentrate comprising an active ingredient and a pH indicator for colouring the water, the proportions of active ingredient and pH indicator in the concentrate being selected so that when the concentrate is diluted with water to provide an effective concentration of active ingredient in the water, the pit indicator indicates visually whether or not the pH of the water is suitable for acceptable agricultural activity of the agricultural chemical.

The invention accordingly applies to agricultural chemicals which have an agricultural activity which varies with the pH of water in the sense that they are sensitive to degradation under alkaline or acid conditions, owing e.g. to hydrolysis thereof under alkaline conditions. When these compositions are used, for example in areas where the water supply such as dam/river water has a pH unsuitable for the agricultural chemical in question, e.g. hard waters which are too alkaline, the farmer or other user typically modifies the pH of the water whereby the agricultural chemical is diluted, so that the water is in an acceptable and preferably optimum pH range to ensure optimum or at least acceptable agricultural activity of the chemical in question. This is effected by adding to the water a suitable adjuvant, e.g. an acid adjuvant when the water is too alkaline. For most agricultural chemicals which are alkali sensitive or acid sensitive, there is a body of learning in connection with the optimum or at least acceptable pH range for good agricultural activity of the chemical in question. Typically the pH of the water supply is measured, and a suitable quantity of adjuvant is added to the water to obtain the desired pH. Field staff must accordingly be equipped to carry out the work involved, e.g. with pH meters, pH indicators (pH sensitive paper or chemicals) or the like, which pH meters can be expensive, bulky and inconvenient, and pH strips can degrade and become unreliable with excessive temperatures. The present invention accordingly seeks to avoid pH determinations or measurements, and to provide for automatic and immediate visual identification of the desired or an acceptable pH during preparation of the agricultural composition.

Typically, the concentrate will contain water as a diluent to facilitate handling and measurement of the concentrate and to dissolve or disperse the various ingredients therein.

The concentrate may thus contain water, being a liquid, the active ingredient being an agricultural adjuvant for enhacing the activity of an agricultural chemical in an aqueous chemical composition. This adjuvant will typically be a pH modifying agent selected from the group comprising acids, alkalis and buffers for controlling and modifying the pH of water.

For use in areas where the available water, such as ground/borehole water or river water is alkaline, the adjuvant may be an acid selected from the group comprising acetic acid, orthophosphoric acid and citric acid, and, although less preferred, hydrochloric acid, sulphuric acid, nitric acid or formic acid.

Naturally, if the available water is too acid, an alkaline pH modifying agent will be employed, e.g. a member of the group comprising ammonia, potassium hydroxide and sodium hydroxide.

In certain cases the adjuvant may in fact be a buffer, being a member of the group comprising ammonia, mono ammonium phosphate, monopotassium phosphate, phosphoric acid, sodium acetate and potassium hydrogen phthalate. In this case the concentrate may, in addition to the buffer, also comprise an agricultural chemical whose agricultural activity varies with the pH of water with which it is in contact and whose agricultural activity is acceptable in the pH range to which the buffer buffers water to which it is added. Admixing of this concentrate with water will automatically, within limits, show whether or not the eventual composition is within an acceptable pH range.

Instead, the concentrate may comprise, in addition to the buffer, an acid or alkali for modifying the pH of water, the buffer serving to guard against excessive pH modification arising from overdosing with the concentrate.

Instead of being an adjuvant, the active ingredient in the concentrate may be an agricalatural chemical whose agricultural activity varies with the pH of water with which it is in contact.

In this case, the concentrate may again contain water, being a liquid, the active ingredient being an agricultural chemical whose activity varies with the pH of water with which it is in contact. In this case, in preparing the agricultural composition from the concentrate, the concentrate will be added to the water, and a separate adjuvant will typically be used, if necessary, in advance to modify the pH of the water to the desired value. Field staff will know in advance, from prior experimentation or usually from manufacturer's specifications and/or official regulations, what concentration of active ingredient is necessary for the agricultural composition in question, i.e. its appropriate dilution in water. The proportion of pH indicator in the concentrate will accordingly be related to the proportion of active ingredient therein so that, when an appropriate mount of concentrate is added to water in preparing the agricultural composition to provide the agricultural composition with the intended concentration of active ingredient, the composition will automatically contain a sufficient proportion of pH indicator for easy visual pH determination. The pH indicator in turn will be chosen so that it can indicate, e.g. by undergoing a colour change or by having a distinctive colour at a suitable pH, when the desired or an acceptable pH has been attained. Field staff accordingly my simply add the appropriate or prescribed amount of the concentrate to the water, and, thereafter, add progressively increasing amounts of the appropriate adjuvant to the water until the colour change takes place, or the appropriate colour is attained.

In this case, ie when the concentrate contains the agricultural chemical whose activity varies with the pH of water with which it is in contact, the active ingredient may be selected from the group comprising pesticides, defoliants, desiccants and plant nutrients. Naturally, a pH colour indicator will be selected which is compatible or inert as regards the other constituents of the concentrate, in particular the agricultural chemical in the concentrate.

The active ingredient may be a pesticide, selected from the group comprising insecticides, nematocides, fungicides and herbicides; and possibly molluscicides and rodenticides. More particularly, the active ingredient may be selected from the group comprising organophsophates, carbamates, benzimidazoles dicarboxamides, bipyridols, pyrethroids and chlorinated hydrocarbons. Typical examples are azinphos methyl, benomyl, captan, dimethoate, ethyl parathion, methomyl, trichlorfon, oxamyl, dibrom, dimecron, mevinphos, monocrotophos, paraquat diquat, cypermethrin and dicofol. Of these, azinphos methyl, dimethoate, ethyl parathion, trichlorfon, dibrom, dimecron, mevinphos and monocrotophos are organophosphates; methomyl and oxamyl are carbamates; benomyl is a benzimidazole; captan is a dicarboxamide; paraquat and diquat are bipyridols; cypermethrin is a pyrethroid; and dicofol is a chlorinated hydrocarbon.

It should be noted that many agricultural chemicals have optimum agricultural activity in a slightly acidic pH range of e.g. pH 4–6.

The pH indicator may be selected from the group comprising methyl red, resorcin blue, 2,5-dinitrophenol and chlorophenol red. The Applicant has found that a pH indicator which can be employed for a large range of agricultural chemicals is methyl red in free base form, such as that available from the Applicant under the trademark Colorite One formulation is a 0.1% m/m solution of methyl red in free base form, in an isopropyl alcohol solvent. This pH indicator changes from colourless at a neutral pH of 7 (sometimes through a yellow stage) to pink in a pH range of about 5.5–about 4.5, and to bright red at a pH of about 4.5 and lower.

Resorcin blue changes from red at pH 4.4 to blue at pH 6.4; 2,5-dinitrophenol changes from colourless at pH 4 to yellow at pH 5.4; and chlorophenol red changes from yellow at pH 4.8 to red at pH 6.4.

The invention extends to a method of preparing an aqueous agricultural composition for application to crops, soil or animals, and which contains an agricultural chemical whose agricultural activity varies with the pH of water with which it is in contact, the method comprising admixing, with the water, a concentrate as described above and the agricultural composition, and effecting such pH modification to the composition as is necessary to obtain a pH in the composition at which said agricultural activity is acceptable.

Any pH modification should preferably take place before the agricultural chemical is added to the mixture. This prevents degradation of the chemical prior to modification of the pH, and avoids any colour masking of the pH indicator hi the mixture by the agriculatural chemical.

The concentrate may comprise an adjuvant which is a pH modifying agent, so that adding the concentrate to the mixture acts to modify the pH of the composition, the agricultural chemical being added separately to the mixture, and subsequently to the addition of the concentrate.

Instead, the concentrate may comprise the agricultural chemical, so that adding the concentrate to the mixture acts to provide an agriculturally effective concentration of said chemical in the composition, any pH modification being effected prior to addition of the agricultural chemical, by adding a separate pH modifying agent to the mixture. Naturally, if it turns out that the water supply is initially at a suitable pH, no pH modification will be required.

In the case described above where the concentrate contains both a buffer adjuvant and an agricultural chemical whose agricultural activity varies with the pH of water with which it is in contact, and whose agricultural activity is acceptable in the pH range to which the buffer buffers water to which it is added, the concentrate may merely be admixed into the appropriate amount of water to prepare the intended agricultural composition. When the concentrate has been added to water in proportions sufficient to provide it with the intended agricultural activity, sufficient buffer will simultaneously and automatically be added to buffer the water to the appropriate pH range, and sufficient pH indicator will automatically be added to confirm that the water is in this pH range. The proportions of pH indicator and buffer will thus be set in the concentrate bearing these requirements in mind and bearing in mind the nature of the agricultural chemical in the concentrate. In this case, it is contemplated that, only with available waters of extremely high or extremely low pH ranges, will the buffer be unable to buffer the water to the appropriate pH range for good agricultural activity of the agricultural chemical, and in these exceptional cases the pH indicator will indicate that suitable buffering has failed to take place.

For a large number of agricultural chemicals which are subject to degradation at unsuitable pH's, an acceptable or desirable pH range is the pH range of 4–6. Methyl red has two colour changes within this range and is accordingly suitable for a large number of agricultural chemicals, a pink colour indicating a suitable pH in the eventual agricultural composition.

It will be appreciated that the present invention is applicable to large numbers of agricultural chemicals and that the concentrations of these chemicals can vary substantially in the eventual formulated agricultural composition for application to crops, soil or animals, depending, inter alia, on the nature of the agricultural chemical itself, the purpose for which it is being used, climatic conditions, the half-life of the agricultural chemical in water of a particular pH, frequency of application, the type of crop, environmental factors and economics, or the like. In each case, the proportion of pH indicator included in the concentrate will be related to the proportion of agricultural chemical therein, merely according to the criterion that sufficient pH indicator should be present when the concentrate has been added to water in the appropriate or intended dilution for the agricultural chemical, so that the pH indicator will be effective and visible at its dilution in the water. In other words, when small amounts of concentrate will be added to water, the proportion of pH indicator in the concentrate will be high, and when large amounts of concentrate are added to water, the proportion of pH indicator therein can be correspondingly lower. For the manufacturer of the concentrate, who will be aware of its intended use and who will prescribe the concentrations at which it will be used, it will be a simple matter to ensure that the concentrate contains sufficient pH indicator to be effective when the concentrate is used at these prescribed concentrations. Considerable and indeed radical variations in the proportions between the agricultural chemical and pH indicator in the concentrate are thus contemplated by the invention, and indeed the absolute concentrations of the agricultural chemical and pH indicator in the concentrate can also vary radically. The Applicant has found, however, that no difficulty is presented in determining such absolute concentrations and relative concentrations, by means of routine experimentation. The proportion of pH indicator in the concentrate may thus vary considerably from one concentrate to another, depending on how much of the concentrate is intended to be added to water. Similar considerations apply when the concentrate contains an adjuvant rather than an agricultural chemical.

Naturally, the agricultural composition, whether it contains an adjuvant and/or an agricultural chemical, may also contain constituents such as spreaders, wetters or the like, such as those typically employed when the eventual agricultural composition is intended for foliar application, or spraying or dipping animals.

The invention will now be described, by way of non-limiting illustration, with reference to the following non-limiting Examples:

Acid adjuvants suitable for pH reduction, control and/or buffering in aqueous agricultural compositions for application to plants or soil and containing alkali-sensitive agricultural chemicals subject to degradation in alkaline environments were formulated to have the following compositions:

EXAMPLE 1

| Constituent | Parts by mass |
| --- | --- |
| Nonyl phenoxy polyoxy-ethylene glycol having 9–10 mole % of ethylene oxide (Wetting Agent) | 10.4 |
| A mixture of the monoortho-phosphoric esters and diorthophosphoric esters of said nonylphenoxy polyoxyethylene-glycol (Buffer) | 43.6 |
| Orthophosphoric acid (Acid Adjuvant) | 2.9 |
| Isopropyl alcohol (Solvent and wetting agent) | 15.6 |
| Water | 25.6 |
| Oleic acid (Acid Adjuvant) | 1.8 |
| Colorite (pH Indicator) | 0.1 |

EXAMPLE 2

| Constituent | Parts by mass |
| --- | --- |
| Acetic acid (Acid Adjuvant) | 77.1 |
| Ammonia (as acetate or amide) (Buffer) | 7.3 |
| Water | 15.5 |
| Colorite (pH Indicator) | 0.1 |

In Example 2 the acetate or amide ammonium salt added was added in a proportion equivalent to 7.3 parts by mass ammonia.

It was found that, when these adjuvants were used to control or maintain the pH of various aqueous mixtures for application to plants or soil and containing alkali-sensitive agricultural compositions (insecticides, fungicides, herbicides, defoliants or the like) subject to degradation, use of the adjuvants in the usual quantities for pH control, adjustment or maintenance in the mixtures provided mixtures whose pH could easily be visually determined by their colour, ie colourless or yellowish at pH's above 5.5, pink in the pH range 5.5 to 4.5 and bright red at pH's below 4.5.

It is an advantage of the invention that it provides a rapid and accurate method of making and/or maintaining an aqueous agricultural chemical composition at its optimum pH range and promotes stability of the chemical and optimal agricultural efficacy with alkaline waters. Moreover, field staff are saved the necessity of calculating the precise amount of adjuvant to be added to the composition, and need not be skilled.

It is a further advantage of the invention when the colouring agent is employed in an agricultural composition other than an adjuvant, ie one whose active ingredient is subject to degradation, that it will indicate if the water supply is in fact within a desired or optimum pH range and does not require pH adjustment.

We claim:

1. A concentrate comprising a mixture of a pH indicator for coloring water, an agricultural chemical for application to crops, soil or animals, and a pH modifying agent for modifying pH of water with which the concentrate is diluted, the agricultural chemical having an activity that varies with the pH of the water and having an acceptable agricultural activity at a pH within the range of 4–6, wherein the proportions of pH modifying agent, pH indicator and agricultural chemical in the concentrate are such that, when the concentrate is diluted with water to provide an effective concentration of the agricultural chemical and the pH of the water is modified by the pH modifying agent, the pH indicator indicates visually when the pH of the water is in the range of 4–6.

2. A concentrate as claimed in claim 1, in which the agricultural chemical is a compound selected from the group consisting of pesticides, defoliants, desiccants and plant nutrients.

3. A concentrate as claimed in claim 2, in which the agricultural chemical is a pesticide selected from the group consisting of insecticides, nematocides, fungicides and herbicides.

4. A concentrate as claimed in claim 3, in which the agricultural chemical is a compound selected from the group consisting of organophosphates, carbamates, benzimidazoles, dicarboximides, bipyridols, pyrethroids and chlorinated hydrocarbons.

5. A concentrate as claimed in claim 4, in which the agricultural chemical is a compound selected from the group consisting of azinphos methyl, benomyl, captan, dimethoate, ethyl parathion, methomyl, trichlorfon, oxamyl, dibrom, dimecron, mevinphos, monocrotophos, paraquat, diquat, cypermethrin and dicofol.

6. A concentrate as claimed in claim 1, in which the pH modifying agent comprises an agricultural adjuvant for enhancing the activity of the agricultural chemical in an aqueous agricultural composition.

7. A concentrate as claimed in claim 6, in which the pH modifying agent is selected from the group consisting of acids, alkalis and buffers for controlling or modifying the pH of water.

8. A concentrate as claimed in claim 7, in which the pH modifying agent comprises an acid selected from the group consisting of acetic acid, orthophosphoric acid and citric acid.

9. A concentrate as claimed in claim 7, in which the pH modifying agent comprises a buffer selected from the group consisting of ammonia, monoammonium phosphate, monopotassium phosphate, phosphoric acid, sodium acetate and potassium hydrogen phthalate.

10. A concentrate as claimed in claim 1, in which the pH indicator comprises a member selected from the group consisting of methyl red, resorcin blue, 2,5-dinitrophenol and chlorophenol red.

11. A concentrate as claimed in claim 10, in which the pH indicator comprises methyl red in free base form.

12. A concentrate as claimed in claim 4, in which the pH modifying agent comprises an acid selected from the group consisting of acetic acid, orthophosphoric acid and citric acid.

13. A concentrate as claimed in claim 12, in which the pH modifying agent comprises a buffer selected from the group consisting of ammonia, monoammonium phosphate, monopotassium phosphate, phosphoric acid, sodium acetate and potassium hydrogen phthalate.

14. A concentrate as claimed in claim 12, in which the pH indicator comprises a member selected from the group consisting of methyl red, resorcin blue, 2,5-dinitrophenol and chlorophenol red.

15. A concentrate as claimed in claim 13, in which the pH indicator comprises a member selected from the group consisting of methyl red, resorcin blue, 2,5-dinitrophenol and chlorophenol red.

16. A concentrate as claimed in claim 14, in which the agricultural chemical is a compound selected from the group consisting of azinphos methyl, benomyl, captan, dimethoate, ethyl parathion, methomyl, trichlorfon, oxamyl, dibrom, dimecron, mevinphos, monocrotophos, paraquat, diquat, cypermethrin and dicofol.

17. A concentrate as claimed in claim 15, in which the agricultural chemical is a compound selected from the group consisting of azinphos methyl, benomyl, captan, dimethoate, ethyl parathion, methomyl, trichlorfon, oxamyl, dibrom, dimecron, mevinphos, monocrotophos, paraquat, diquat, cypermethrin and dicofol.

18. The concentrate of claim 1, wherein said agricultural chemical is subject to degradation outside of said pH range of 4–6.

19. A process for preparing an agricultural composition which is suitable for application to crops, soil or animals, comprising:

(a) providing a concentrate comprising a mixture of a pH indicator for coloring water, an agricultural chemical for application to crops, soil or animals, and a pH modifying agent for modifying pH of water with which the concentrate is diluted, the agricultural chemical having an activity that varies with the pH of the water and having an acceptable agricultural activity at a pH within the range of 4–6, wherein the proportions of pH modifying agent, pH indicator and agricultural chemical in the concentrate are such that, when the concentrate is diluted with water to provide an effective concentration of the agricultural chemical and the pH of the water is modified by the pH modifying agent, the pH indicator indicates visually when the pH of the water is in the range of 4–6; and (b) diluting said concentrate with water so as to effect a color change of the pH indicator of said concentrate.

20. The process of claim 19, wherein in said providing step, said agricultural chemical is a compound selected from the group consisting of azinphos methyl, benomyl, captan, dimethoate, ethyl parathion, methomyl, trichlorfon, oxamyl, dibrom, dimecron, mevinphos, monocrotophos, paraquat, diquat, cypermethrin and dicofol; said pH modifying agent includes an acid selected from the group consisting of acetic acid, orthophosphoric acid and citric acid, and further includes a buffer selected from the group consisting of ammonia, monoammonium phosphate, monopotassium phosphate, phosphoric acid, sodium acetate and potassium hydrogen phthalate; and said pH indicator includes a member selected from the group consisting of methyl red, resorcin blue, 2,5-dinitrophenol and chlorophenol red.

* * * * *